United States Patent [19]

Naim et al.

[11] Patent Number: 5,595,189
[45] Date of Patent: Jan. 21, 1997

[54] METHODS AND APPARATUS FOR MEASURING BODY COMPOSITION

[75] Inventors: Ari B. Naim, Philadelphia; Stephen Dubin, Springfield; Beth A. Schrope, Philadelphia, all of Pa.

[73] Assignees: Reshet, Bala Cynwyd; Drexel University, Philadelphia, both of Pa.

[21] Appl. No.: 484,595

[22] Filed: Jun. 7, 1995

[51] Int. Cl.$^6$ ............................................. A61B 5/103
[52] U.S. Cl. ................................. 128/774; 73/433
[58] Field of Search ............................ 128/774; 73/149, 73/433

[56] References Cited

U.S. PATENT DOCUMENTS

| | | | |
|---|---|---|---|
| 3,487,698 | 1/1970 | Leger, Jr. et al. | 73/433 |
| 3,557,625 | 1/1971 | Leger, Jr. et al. | 73/432 |
| 3,769,834 | 11/1973 | Fletcher et al. | 73/149 |
| 4,144,749 | 3/1979 | Whitmore | 73/149 |
| 4,144,763 | 3/1979 | Vogelman | 73/433 |
| 4,184,371 | 1/1980 | Brachet | 73/433 |
| 5,052,405 | 10/1991 | Batchelder | 128/774 |

FOREIGN PATENT DOCUMENTS

| | | | |
|---|---|---|---|
| 2455389 | 6/1975 | Germany | 73/433 |
| WO89/084328 | 9/1989 | WIPO . | |
| WO92/00700 | 1/1992 | WIPO . | |

*Primary Examiner*—Max Hindenburg
*Assistant Examiner*—Pamela L. Wingood
*Attorney, Agent, or Firm*—Woodcock Washburn Kurtz MacKiewicz & Norris

[57] ABSTRACT

A system for measuring body fat percentage is disclosed. The system relies upon the measurement of a subject's weight in two gases of different densities. The difference in weight, along with the difference in atmospheric density, is used to determine the subject's density. Implementing Archimedes' principle of binary mixtures, this figure is used to determine the proportion by weight of fat in the subject. The weight of the subject is measured with a precision balance. The density of the gas is determined with an ultrasonic probe that senses the change in sonic velocity, which is related to the density of the atmosphere.

25 Claims, 2 Drawing Sheets

METHODS AND APPARATUS FOR MEASURING BODY COMPOSITION

FIELD OF THE INVENTION

The present invention relates generally to methods and apparatus for measuring body composition, and more particularly relates to methods and apparatus for measuring percent body fat.

BACKGROUND OF THE INVENTION

There are numerous methods for measurement of body composition. A recent review article lists some twenty-three distinct methods being used or investigated for the estimation of body fat percentage. See Brodie, D. A.: *Techniques of measurement of body fat composition*, Sports Medicine 1988; 5:11–40 (Part I) and 5:74–98 (Part II); Forbes, G. B. (1987) *Human Body Composition*, New York, Springer-Verlag. This large list of methods demonstrates the importance of this measurement in medical practice and research.

Several problems arise in the evaluation and comparison of methods for the estimation of body fat percentage. For example, some of the nomenclature is ambiguous. The total body electromagnetic conductivity (TOBEC) method is distinct from the electrical impedance method, although they are often confused. All methods except direct carcass analysis depend upon the assumption of being robust in the face of inhomogeneity of location of the body components being measured. In the case of adipose tissue, this may be exemplified by the well known differences in fat distribution between men and women, during growth and development, and among ethnic populations. Perhaps less well recognized are the effects of differences in the general body conformation and varying distribution of blood, respiratory and enteric gas volumes. When used with inhomogeneous distributions of the body components being measured, the only truly robust body composition measurement methods are hydrostatic weighing and analogous methods.

Many methods, such as the electrical impedance and skin fold methods, require an indirect calibration through mathematical correlation with a criterion method or regression formula. Such a calibration can never be more precise than the hydrostatic weighing method. When they contain terms for weight and height and are sex, age and somatotype specific, regression formulas may actually contain little information about the method being evaluated. The test of statistical significance for a correlation coefficient (r) is surprisingly lenient, particularly for large experimental samples. With the number of samples (N) greater than 120, r need only be greater than 0.125 to achieve a probability (p) less than 0.05. Thus an investigator can report a "highly significant linear correlation" even when the data has little real value.

Hydrostatic Weighing is a direct extension of Archimedes' principle. The subject is weighed while immersed totally in water, and asked to exhale to remove as much of the air in his body as possible for a period of 90 seconds. The average density of adipose tissue (~0.9) and that of lean body mass (1.10) have been determined by various analytical means. Using these values, the analogous formula for percentage body fat (x) as a function of density (d) is:

$$\frac{100}{d(\text{body})} = \frac{100-x}{1.10} + \frac{x}{0.9} \tag{1}$$

-continued
$$x = \frac{495}{d(\text{body})} - 450$$

Because it is founded upon direct and well known physical principles without a need for indirect calibrations or limiting assumptions, hydrostatic weighing has become the "gold standard," or criterion method, for use in human subjects. However, one disadvantage of hydrostatic weighing is that it requires a very cooperative subject. Therefore, it is not suitable for babies or elderly, ill or physically challenged persons, or for comparative studies of other species. In addition, residual air in the lungs is a source of error.

Direct Carcass Analysis is the comparable criterion method for laboratory animals. In this ultimately invasive procedure, the subject is physically homogenized so that an aliquot sample can be subjected to extraction with an organic solvent. In addition to the death of the subject, the disadvantages of this method include the need for dangerous solvents and the availability of only one data point per subject.

Skin fold calipers and anthropometrics is the most commonly applied clinical method for men and women. This method uses measurements of skinfold thicknesses taken at the waist, chest and hip girth. This method is non-invasive, uses inexpensive apparatus, and is useful when performed by trained operators. However, anthropometric methods generally assume that the ratio of subcutaneous and other fat is constant within the group, and thus are limited to relatively homogeneous groups (e.g., young female gymnasts or young male weight lifters).

Electrical Impedance Measurement by current injection has received much recent interest, especially in the context of athletics and fitness programs. Electrical current at about 50 kHz is injected through electrodes on the subject's limbs to deduce electrical impedance. The subject is connected to a measuring device through four electrodes (usually two on an arm and two on the ipsilateral leg) and the electrical impedance is deduced from the voltage appearing on two passive electrodes when an electrical current at about 50 kHz is injected through the active electrodes. Although significant correlation with criterion methods has been claimed for this method, careful examination of these studies reveals these disturbing factors:

(1) The coefficients for the regression formulas for humans show that the contribution of the impedance to the calculation of fat percentage is actually rather small. Furthermore, the coefficient for the term(s) involving impedance varies widely among studies. The investigators recommend that age, sex and "fatness" specific formulas be used. In an isolated study where such additional sources of information were not used—a study in chickens where direct carcass analysis was the criterion method—the correlation coefficient was only 0.71, indicating that only half of the variation in body fat was "explained" by the impedance.

(2) A recent study (Burkholder, W. (1991) Research Presentation) in dogs showed a very large (~40%) increase in body impedance during measurement under general anesthesia. This change was well correlated with rather moderate (~3 degrees F.) body temperature decrease and points to an important effect of changes in blood distribution in addition to vulnerability to inhomogeneity of fat deposition. The equipment is rather expensive and must be carefully designed to avoid danger from currents through the body. Additional limitations in nonhuman animals include hair, movement and extreme sensitivity to body conformation.

Total Body Electromagnetic Conductivity (TOBEC) is quite distinct from impedance measurement using current injection. With TOBEC, the subject is exposed to microwave energy in a chamber and the percentage body fat is assumed to be related to the differential absorption of microwave energy by fat and lean body mass. The raw TOBEC number is related to actual fat percentage using a regression formula. A controversial feature of this method is the large difference in TOBEC numbers as found in the same animals immediately before and after death. This change is directly related to changes in body temperature and is probably related to changes in blood distribution. Another disadvantage of this method is that the apparatus is expensive (more than $50,000 for human child size).

Total Body Water methods use administration of materials such as deuteriated or tritiated water, antipyrine, etc., which are assumed to be well and exclusively distributed in the "water space" of the body. Computations are based on assumptions about the relative distribution of water in the fat and lean body mass and assumptions about the distribution, fate and excretion of these materials. Correlation of these methods with hydrostatic weighing in adult healthy humans is good but correlation with criterion methods for animals is only marginal. This indicates that the computational model must be reformulated for each species and patient type. Some of the analytical methods are expensive and prolonged housing in metabolism cages is required for animals.

Total Body Potassium is a method based upon the relative distribution of potassium and its radioactive isotopes in the body water. The patient/subject is "counted" with a total body scintillation counter. The subject must be still for more than five minutes and body geometry factors are very important. In adult humans, the correlation with criterion methods is good. However, comparisons have not been reported in non-human animals. Furthermore, this method is tedious and the apparatus is very expensive.

U.S. Pat. No. 5,052,405, Oct. 1, 1991, titled "Method and Apparatus for Measuring the Density of an Object Including a Living Being," discloses a system based on Archimedes' principle for measuring the density of an object or living being. In this patent, the substance or subject is enclosed in a chamber and the temperature of the surrounding air is changed to vary its density. The apparent weight change of the subject at the different temperatures represents the change in the buoyant force exerted by the air on the subject. The buoyant force can then be calculated from the volume of the subject determined from its relationship with the buoyant force. The density of the subject can then be calculated from the volume and weight parameters and related directly to fat content. One disadvantage of this method is that it is constrained by the variation in temperature needed to produce a significant change in air density and buoyant force. Take, for example, a 70 kg subject with 25% body fat being measured at 55% relative humidity and 760 mmHg barometric pressure. A temperature change from 40° C. (100° F.) to 0° C. (32° F.) results in a weight differential of 10.96 g, i.e., only a 0.016% change. Therefore, this method is not useful for living subjects or any temperature sensitive substances.

International Patent Application PCT/US/W089/08428 discloses a method of measuring fat percentage using infrared absorption, which only sees the surface of a fatty region and offers very low accuracy.

U.S. Pat. No. 4,831,527 discloses a method in which tissue elasticity, pronounced in the stomach and buttocks, is used to produce variations in weight after an abrupt movement by a subject. The upward and downward forces caused by the movement of the stomach and buttocks are then correlated to overall fat percentage. This method is obviously highly dependent on fatty tissue location.

A number of patents (U.S. Pat. Nos. 4,449,406; 3,455,168; 3,557,625; and 3,487,698) describe methods for measurement of fat percentage in meat and are not suitable or adaptable for living subjects.

A series of patents have approached volumetric measurement of subjects as a means of arriving at body composition. U.S. Pat. No. 4,184,371 and U.S. Pat. No. 4,144,763 describe methods that do not account for the air volume in the lungs, resulting in significant inaccuracies. In U.S. Pat. No. 3,769,834, there is an attempt to deal with the respiratory error effects, but the method disclosed in the patent produces a large acoustic leak through tissue coupling from the chamber to the airways to the outside of the chamber. U.S. Pat. No. 4,369,652 describes a method that better accounts for lung volume but requires the subject to be wrapped in a down or polyester cocoon. In addition, this method requires elaborate precautions to control temperature.

In sum, the "gold standard" for measuring body composition in terms of fat percentage is underwater weighing based on measuring the density of the subject. Underwater weighing requires a fit cooperative subject as well as a tank of water adequate for total immersion. However, this method is clearly unsuited for small children, sick people or non-human animals. As discussed above, numerous other methods have been developed but these suffer from danger, discomfort, lack of precision, impracticality and great expense.

SUMMARY OF THE INVENTION

An object of the present invention is to provide a safe, precise and pleasant measurement of body composition. Briefly, according to the present invention, the physical and chemical properties of the atmosphere of an enclosing chamber are manipulated. The subject's volume is determined by measuring the differential buoyancy acting on the subject in light (low density) and heavy (high density) atmospheres. The atmosphere to which the subject is exposed is safely and pleasantly breathable—consisting only of oxygen and various inert gases.

One preferred embodiment of the present invention includes measuring the density of a subject. The percent body fat of the subject may then be estimated on the basis of the subject's density. The inventive method includes the steps of: weighing the subject in a first gaseous atmosphere having a first density, the first gaseous atmosphere being safely breathable by the subject and being composed of a first mixture of gases; weighing the subject in a second gaseous atmosphere having a second density, the second gaseous atmosphere being safely breathable by the subject and being composed of a second mixture of gases different from the first mixture of gases; and estimating the subject's density on the basis of a difference in weight of the subject in the first and second atmospheres.

Preferably, the difference in atmospheric density between the first and second gas mixtures will be as large as possible. One presently preferred combination of gases is where the first atmosphere is composed of 80% He and 20% $O_2$, and the second atmosphere is composed of 80% sulfur hexafluoride ($SF_6$) and 20% $O_2$. In preferred embodiments of the invention, the temperature of the first atmosphere is approximately the same as the temperature of the second atmosphere. Preferably, the barometric pressure, atmospheric pressure and humidity remain constant throughout the measurement process. Preferred embodiments also include the steps of measuring the densities of the first and second atmospheres in real time, wherein the step of estimating the subject's density includes estimating the subject's density on the basis of the measured densities of the first and second atmospheres.

Since the inventive approach disclosed herein does not require the cooperation of the patient or subject and poses no stress or danger, it has a much broader applicability to medical diagnosis and human and animal research than current methods. Athletic and fitness programs have also demonstrated a need for such an approach, as health awareness is becoming prevalent. The inventive approach has the advantage over hydrostatic weighing of not requiring measurement of residual air in the lungs. Thus, a source of error and/or labor is eliminated. The invention has been tested on animals and exhibited precision comparable or better than other non-destructive methods. The invention has been applied to conscious animals with no apparent harm or discomfort.

The present inventors have devised an ultrasonic instrument that facilitates measurement of atmospheric density in the enclosure during weighing. This improves the precision of the body fat measurement and removes the need for a rigid enclosure. Continual precise measurement of density also means that the measurement process (exchange of gases in the enclosure, exponential in rate) can be stopped as soon as the atmospheric density in the chamber has changed enough to provide an acceptably accurate measurement. The amount of inert gas usage and time required per measurement can be minimized, facilitating cost reduction and quick measurement repetition if desired. In this fashion, the density measurement is used as a control parameter (regulator) in automating the entire system. Other density measurement methods currently available on the market can be used in place of the one discussed here, and therefore the present invention is by no means limited to the use of the density measurement method disclosed herein.

The preference for constant humidity, temperature and atmospheric pressure is a consequence of the desirability of reducing or eliminating the effect evaporation of moisture on the subject has on the accuracy of the final measurement. The need to maintain constant humidity, temperature and atmospheric pressure can be removed with the addition of humidity, temperature and atmospheric pressure sensors. Information from such sensors may be incorporated in real-time into the measurement calculation to compensate for the effects of evaporation.

Other features and advantages of the present invention are disclosed below.

DETAILED DESCRIPTION OF PREFERRED EMBODIMENTS

Archimedes' principle is the basic principle upon which the present invention is based. This principle states that:

(1) The weight of any object will be opposed by a (buoyant) force equal to the weight of the enclosing medium displaced by the object. From this, the volume and density of the object may be deduced.

(2) The density of any binary (two part) mixture will be the sum of the densities of the pure components each weighted by the proportion of the corresponding component.

Thus, if one knows the density of an object—as determined from its weight and volume, and the density of two components of which it is assumed to be composed, the relative percentage of each component may be calculated. The physical principles underlying this method are totally independent of the shape of the object and the homogeneity or lack thereof in the distribution of the components throughout the object.

Figure 1:
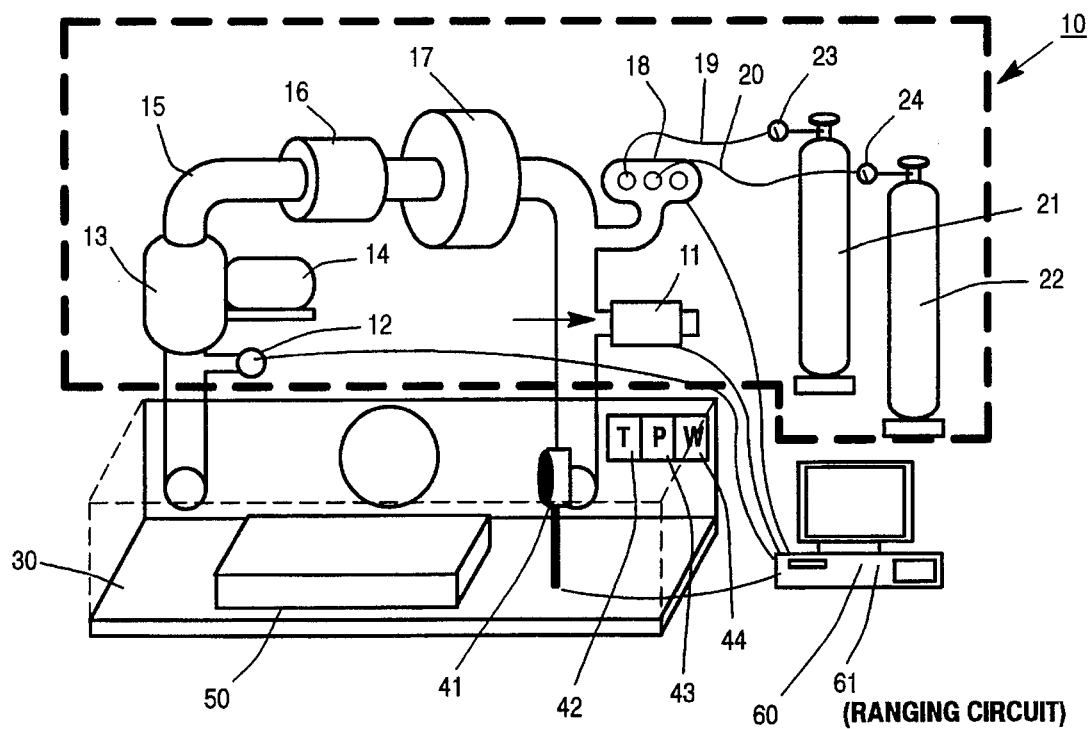
FIG. 1 depicts a differential buoyancy unit in accordance with the present invention.

FIG. 1 illustrates a first embodiment of the present invention. The body composition measurement system includes four key elements: a gas flow control system 10; an ultrasound system for determining gas density, depicted generally at 41, 61; a precision laboratory balance or scale 50 for measuring the mass of the subject; and an enclosure 30 to confine the gas to the measurement site. The enclosure 30 need not be rigid. Sealing the enclosure from loss of gas is not necessary because atmospheric density measurements are performed in real-time with a high degree of accuracy.

Solenoid valves 18 are used to control the flow of gas into the chamber. The valves are connected to the gas cylinders 21 and 22 via regulators 23 and 24, respectively. With the aid of a circulator 14, the gas is directed through a particle filter 17 to remove unwanted or unbreathable substances and then through a carbon dioxide absorber 16 to remove carbon dioxide. These stages are only necessary if the gas is recycled to conserve the amount of gas expended per weighing session. The gas is then tested for oxygen composition by an oxygen sensor 12 to ensure the safety of the subject.

The scale 50 is positioned within the enclosure 30 to weigh the subject during the gas exchange process. The scale is chosen to provide the needed accuracy level demanded by the body composition measurement. The accuracy level can be calculated or read from a plot prepared for the weight of the subject being measured. It is important to choose a scale that is unaffected by the changing atmospheric density in the enclosure.

All components of the measurement system can be remotely controlled via a computer 60. The measurements required for the body composition calculation are weight and density. Therefore, direct communication is established between the scale 50 and the ranging circuit 61 to receive real-time data during the measurement process. Concurrently, the computer 60 sends control signals to the solenoid valves 18 to regulate the gas input to the chamber 30. Since the computation of body fat percentage and control of the gas exchange process are performed by the computer 60 in real-time, the computer 60 can also send a stop signal to the valves 18 when a pre-specified level of accuracy is reached. An electrostatic transducer 41 and the ranging circuit 61 are used as the basis for the ultrasound sonic velocity measurement (see FIG. 2 for more detail).

Figure 2:
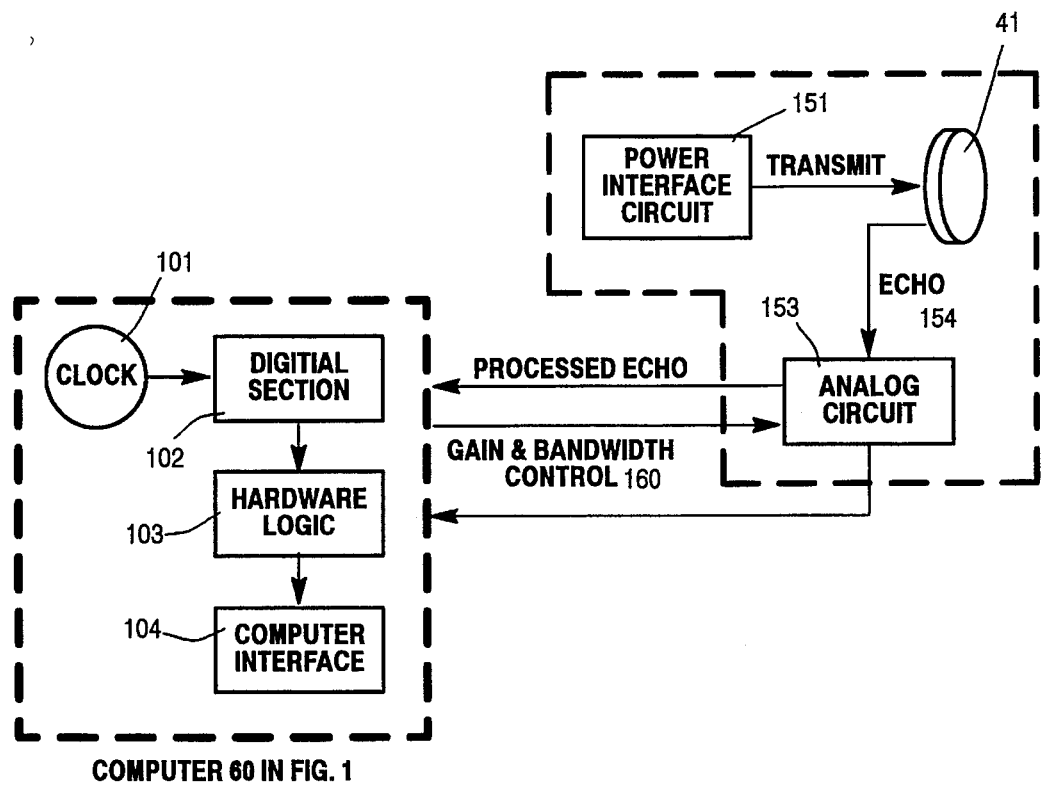
FIG. 2 is a block diagram of an ultrasonic velocity measurement system in accordance with the present invention.

Referring to FIG. 2, the ultrasonic density measurement system includes a transducer 41 (operating, e.g., at 40 kHz) driven by a dedicated power interface circuit 151 in pulse-echo mode (the same unit is used to transmit a pulse and receive its echo), where the reflecting interface is the opposite wall of the chamber 30. The transducer 41 is aligned so that the ultrasonic beam is oriented perpendicular to the reflecting surface, so that maximum signal and true distance directly related to time-of-flight are insured. The returning echo 154 is processed in an analog circuit 153 to increase its signal-to-noise ratio by bandpass filtering the signal around the operating frequency and then amplifying the resulting filtered signal. The processed echo is then passed to a digital section 102 and compared by using a clock 101 to extract the time-of-flight information, from which sonic velocity (and hence gas density) is calculated. Parameters for operation, such as gain and bandwidth control, pulse repetition frequency, averaging, etc., can be set remotely by the computer 60. Typical systems for use in this application are capable of a resolution of 0.066 mm in distance measurement and 0.2 μsec in time resolution. The system also includes hardware logic 103 and a computer interface 104, which may be housed with digital section 102 and clock 101 in the computer 60 (FIG. 1).

Under certain circumstances it may be necessary to account for variations in weight due to water evaporation. To do so, atmospheric temperature, pressure and humidity sensors (42, 43, 44, respectively) are incorporated into the measurement system. The data from these sensors are sent to the computer 60 and employed to correct the body composition calculations.

Method of Operation

The subject is placed on the scale 50 inside enclosure 30. Since density is being measured in real-time, sealing the enclosure is not essential. Care must be taken to choose a scale that is not affected by atmospheric changes (though the scale 50 can be placed beneath the enclosure if such changes pose difficulties).

The rationale for the measurement of body fat percentage by differential buoyancy "in the dry" is analogous to that for hydrostatic weighing. Instead of immersing the subject in water, breathable mixtures of at least 20% oxygen with other inert gases are used. The density and other related measures for several gases and mixtures are given in the table below.

| Gas | Density (gm/l) | Velocity (m/sec) |
|---|---|---|
| Air | 1.293 | 331 |
| Helium | 0.178 | 965 |
| Nitrogen | 1.251 | 334 |
| Oxygen | 1.429 | 316 |
| SF$_6$ | 6.602 | 136 |
| "Light" Air 80% He + 20% O$_2$ | 0.428 | 607 |
| "Heavy" Air 80% SF$_6$ + 20% O$_2$ | 5.567 | 143 |

For any enclosing atmosphere, the apparent weight will be equal to the "true" (in vacuo) weight diminished by a buoyant force equal to the volume of the object being weighed multiplied by the density of the enclosing medium. If an object were weighed in two gaseous atmospheres, one light and one heavy, the volume (V) of the object could be determined from:

$$V = \frac{\text{weight(light gas)} - \text{weight(heavy gas)}}{d(\text{heavy gas}) - d(\text{light gas})} \quad (2)$$

Better precision will be obtained if the body volume is higher or if the density of the enclosing atmospheres is more disparate. Sulfur hexafluoride (SF$_6$), in spite of its forbidding name, is a safely inert gas which is very dense and which has been used in breathing mixtures in numerous animal and human studies. See Forkert, L., Wood, L. D., and Cherniak, R. M.: *Effect of gas density on dynamic pulmonary compliance*, J Appl Physiol 1975; 39:906–910; Maio, D. A., and Farhi, L. E. (1970), *Effect of Gas Density on Mechanics of Breathing*, SAM-TR-70-5, Washington, Tech Rep SAM-TR 15–21; Drechsler, A., Parks, D. M., Larsen, R. W., and Ultman, J. S.: *Inert gas mixing in the upper airways of man*, Respir Physiol 1985; 62:305–324; Kelly, S. et al.: *Gas mixing in the lungs of dogs and pigs*, Resp Physiol 1982; 47:341–349.

The question of the accuracy with which the density of the enclosing medium can be known is a challenging one. Some sources of error are: (1) Variability in the composition of the gas mixtures as supplied; (2) Incomplete mixing and replacement of one atmosphere with another; and (3) Changes of density due to metabolism of the subject or patient through respiratory exchange of oxygen for carbon dioxide and the variability of temperature, barometric pressure and humidity of the atmosphere. Rather than deal with these from a theoretical approach, the density of the enclosing atmosphere is measured at the same time that weighing is performed. The method is derived from the systematic relationship between the density of a gas and the velocity of sound in that medium. See Kinsler, L. E. et al: *Fundamentals of Acoustics* (Ed III), New York, Wiley, 1982. The velocity of sound (c) is given by:

$$c = \sqrt{\frac{\gamma * P_0}{\rho_0}} \quad (3)$$

where $P_0$ represent the equilibrium atmospheric pressure, $\gamma$ represents a constant (ratio of heat capacities), and $\rho_0$ represents the density of the atmosphere. The above relationship was confirmed from published values of the density and sonic velocities of the gases of interest (see *The Merck Manual On-line* and *Kirk-Othmer On-line*, Knowledge Index (Subset of Dialog) Electronics Database System) such that $$\text{sonic velocity} = a + \frac{b}{\sqrt{d}} \quad (4)$$

where a and b are determined from given values of density and sonic velocity. From the relationships in equations (1), (2) and (3), and knowledge of the densities of the homogeneous components, percent composition of two components in a binary mixture, such as percent body fat and a fat/lean mixture can be determined.

Figure 3:
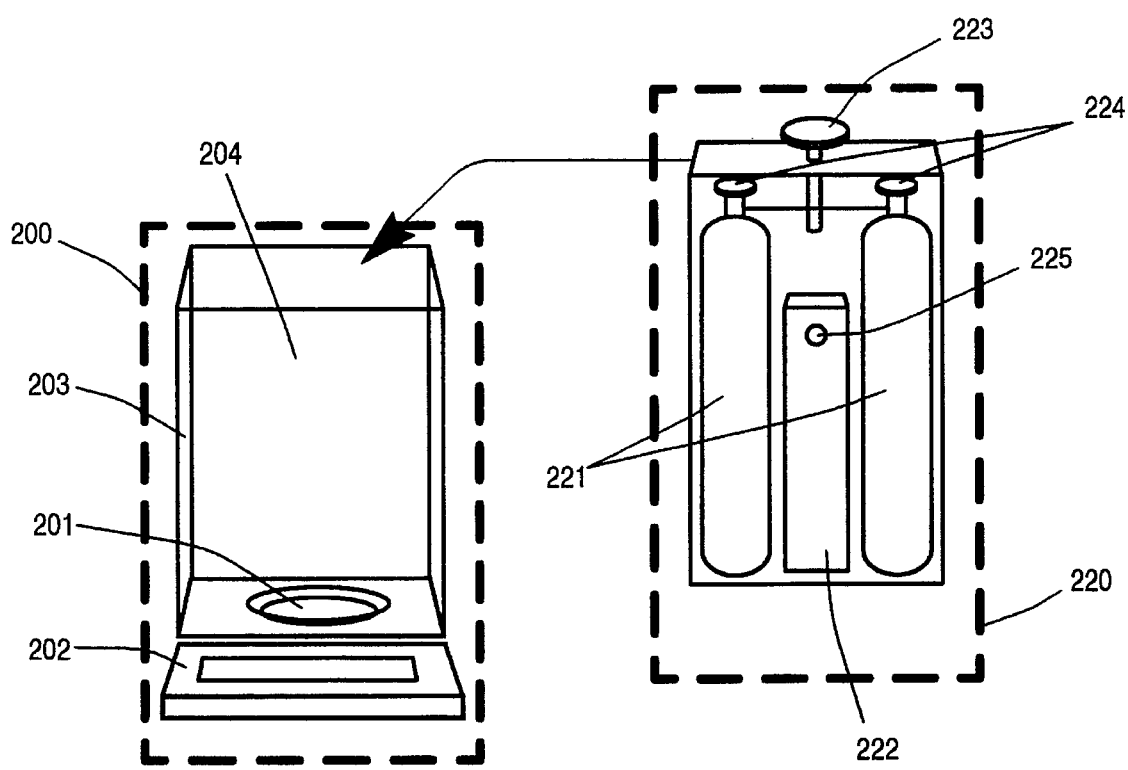
FIG. 3 depicts a density measurement unit mounted on a commercial analytical scale in accordance with the present invention.

Another embodiment of the present invention employs the adaptation of existing weighing devices to incorporate the above-described technology. This concept is depicted in FIG. 3. A commercial analytical scale 200 composed of a weighing pan 201, electronics with weight measurement output 202, and an enclosure 203 to prevent errors due to air currents. A composition measurement unit 220 may be constructed of two tanks 221 of two different gases, or one or two tanks of a single gas (if air is used as one of the two gases in which the weighing is being performed). The tanks 220 are controlled by manual or remote control valves 224. A shutoff 223 provides protection. In addition, an ultrasonic density measurement system 222 comprising a transducer 225 and accompanying electronics is also included.

The composition measurement unit 220 can then be attached to the rear of the commercial device 200. Aside from the mechanical attachment, an electrical attachment can also be implemented easily. The electrical attachment can serve to automate the composition measurement unit 220 by providing the control signal to the gas valves 224 to initiate gas release and then by performing all the necessary calculations in the electronics 202. Care must be taken to fit the gas entry inlet 204 to the gas output of the composition measurement unit 220. The ultrasonic transducer should fit the commercial unit so that a direct reflection is achieved at a precisely known distance.

Calibration of the ultrasonic density measurement system is simple. Since the ultrasonic velocity in air is known with a high degree of accuracy, calibration can be achieved by assuming a known velocity and solving for the distance. This distance can then be used in subsequent measurements to solve for the velocity.

To assure the accuracy of the velocity calibration of the ultrasonic measurement system, the density of the air immediately preceding a measurement process can be measured using other sensory data. Using temperature, barometric pressure and relative humidity measurements, made with sensors attached to enclosure 30, $$D = \frac{M}{RT} \left( P_b - \frac{(M-M_W) P_{SW} H}{100 M_W} \right) \quad (5)$$

$$P_{SW} = 6.11 \, e \left( 25.22 \left( \frac{T-273}{T} \right) - 5.31 \ln \left( \frac{T}{273} \right) \right) \quad (6)$$

where D is the density, M is the molecular weight of the gas, R is the universal gas constant, T is the gas temperature (degrees Kelvin), $P_b$ is the barometric pressure, $M_w$ is the molecular weight of water, $P_{sw}$ is the saturated vapor pressure, and H is the relative humidity (%). For gas mixtures, M is the weighted average of the molecular weights of the components. For air, M is 28.9.

Then, the parameters a and b can be determined from equation (4). If needed, this process can advantageously be performed throughout the measurement process to further improve the accuracy of the fat composition measurement.

It is evident that this method of measuring composition is applicable in many settings primarily because of the ease of performing measurements and its non-invasive nature. Measurement accuracy is limited only by the accuracy of the equipment used to obtain the weight and density values. For an 80 kg subject with body volume of 0.08 m$^3$, errors of 0.02% in velocity and 0.1% in weight measurements result in a 2.5% error in body composition. These figures are for using a heavy gas with a density of 5.567 kg/m$^3$ and a light gas with a density 0.428 kg/m$^3$.

We claim:

1. A method for measuring the density of a subject living, comprising the steps of:
   (a) weighing the subject in a first gaseous atmosphere having a first density, said first gaseous atmosphere being safely breathable by said subject and being composed of a first mixture of gases;
   (b) weighing the subject in a second gaseous atmosphere having a second density, said second gaseous atmosphere being safely breathable by said subject and being composed of a second mixture of gases different from said first mixture of gases; and
   (c) estimating the subject's density on the basis of a difference in weight of the subject in said first and second atmospheres.

2. A method as recited in claim 1, wherein at least one of said first and second atmospheres includes sulfur hexafluoride ($SF_6$).

3. A method as recited in claim 2, wherein said first atmosphere is composed of 80% He and 20% $O_2$, and said second atmosphere is composed of 80% $SF_6$ and 20% $O_2$.

4. A method as recited in claim 1, wherein the temperature of said first atmosphere is approximately the same as the temperature of said second atmosphere.

5. A method as recited in claim 1, further comprising the steps of measuring the densities of said first and second atmospheres in real time, wherein the step of estimating the subject's density includes estimating the subject's density on the basis of the measured densities of the first and second atmospheres.

6. A method as recited in claim 5, wherein the steps of measuring the densities of said first and second atmospheres include measuring the velocity of sound waves in said first and second atmospheres in real time.

7. A method as recited in claim 1, wherein at least one of said first and second atmospheres includes sulfur hexafluoride ($SF_6$); wherein the temperature of said first atmosphere is approximately the same as the temperature of said second atmosphere; and further comprising the steps of measuring the densities of said first and second atmospheres in real time, wherein the step of estimating the subject's density includes estimating the subject's density on the basis of the measured densities of the first and second atmospheres.

8. A method as recited in claim 7, wherein the steps of measuring the densities of said first and second atmospheres in real time include measuring the velocity of sound waves in said first and second atmospheres.

9. A method as recited in claim 8, wherein said first atmosphere is composed of 80% He and 20% $O_2$, and said second atmosphere is composed of 80% $SF_6$ and 20% $O_2$.

10. A method as recited in claim 1, further comprising estimating the percent body fat of the subject on the basis of the subject's density.

11. A method as recited in claim 9, further comprising estimating the percent body fat of the subject on the basis of the subject's density.

12. A system for measuring the density of a subject living, comprising:
    (a) means for weighing the subject in a first gaseous atmosphere having a first density, said first gaseous atmosphere being safely breathable by said subject and being composed of a first mixture of gases;
    (b) means for weighing the subject in a second gaseous atmosphere having a second density, said second gaseous atmosphere being safely breathable by said subject and being composed of a second mixture of gases different from said first mixture of gases; and
    (c) means for estimating the subject's density on the basis of a difference in weight of the subject in said first and second atmospheres.

13. A system as recited in claim 12, wherein at least one of said first and second atmospheres includes sulfur hexafluoride ($SF_6$).

14. A system as recited in claim 13, wherein said first atmosphere is composed of 80% He and 20% $O_2$, and said second atmosphere is composed of 80% $SF_6$ and 20% $O_2$.

15. A system as recited in claim 12, wherein the temperature of said first atmosphere is approximately the same as the temperature of said second atmosphere.

16. A system as recited in claim 12, further comprising means for measuring the densities of said first and second atmospheres in real time, wherein said means for estimating the subject's density includes means for estimating the subject's density on the basis of the measured densities of the first and second atmospheres.

17. A system as recited in claim 16, wherein said means for measuring the densities of said first and second atmospheres includes means for measuring the velocity of sound waves in said first and second atmospheres in real time.

18. A system as recited in claim 12, wherein at least one of said first and second atmospheres includes sulfur hexafluoride ($SF_6$); wherein the temperature of said first atmosphere is approximately the same as the temperature of said second atmosphere; and further comprising means for measuring the densities of said first and second atmospheres in real time, wherein the means for estimating the subject's density includes means for estimating the subject's density on the basis of the measured densities of the first and second atmospheres.

19. A system as recited in claim 18, wherein the means for measuring the densities of said first and second atmospheres in real time includes means for measuring the velocity of sound waves in said first and second atmospheres.

20. A system as recited in claim 19, wherein said first atmosphere is composed of 80% He and 20% $O_2$, and said second atmosphere is composed of 80% $SF_6$ and 20% $O_2$.

21. A system as recited in claim 12, further comprising means for estimating the percent body fat of the subject on the basis of the subject's density.

22. A system as recited in claim 20, further comprising means for estimating the percent body fat of the subject on the basis of the subject's density.

23. A method for measuring the percent body fat of a subject, comprising the steps of:
   (a) weighing the subject in a first gaseous atmosphere having a first density, said first gaseous atmosphere being safely breathable by said subject and being composed of a first mixture of gases;
   (b) weighing the subject in a second gaseous atmosphere having a second density, said second gaseous atmosphere being safely breathable by said subject and being composed of a second mixture of gases different from said first mixture of gases;
   (c) estimating the densities of the first and second atmospheres;
   (d) estimating the subject's density on the basis of the densities of the first and second atmospheres and a difference in weight of the subject in said first and second atmospheres;
   (e) estimating the percent body fat of the subject on the basis of the subject's density.

24. A method as recited in claim 1, wherein the temperature, barometric pressure, and humidity are measured in and used in said estimating step.

25. A system as recited in claim 12, comprising means for measuring the temperature, barometric pressure, and humidity and using the measurements to estimate the subject's density.

* * * * *